(12) United States Patent
Rivera

(10) Patent No.: US 10,980,681 B2
(45) Date of Patent: Apr. 20, 2021

(54) MULTI-LEVEL FIRST AID KIT AND BRACKET

(71) Applicant: George Rivera, Walnut, CA (US)

(72) Inventor: George Rivera, Walnut, CA (US)

(*) Notice: Subject to any disclaimer, the term of this patent is extended or adjusted under 35 U.S.C. 154(b) by 50 days.

(21) Appl. No.: 16/415,880

(22) Filed: May 17, 2019

(65) Prior Publication Data
US 2020/0360201 A1 Nov. 19, 2020

(51) Int. Cl.
*A61F 17/00* (2006.01)

(52) U.S. Cl.
CPC .................. *A61F 17/00* (2013.01)

(58) Field of Classification Search
CPC .......... A45C 3/02; A45C 13/02; A61B 17/00; A61F 17/00
USPC ................. 206/476–482, 557–565, 570–572
See application file for complete search history.

(56) References Cited

U.S. PATENT DOCUMENTS

| | | | | |
|---|---|---|---|---|
| 5,207,325 A | * | 5/1993 | Kennedy | A61L 2/26 206/370 |
| 6,267,484 B1 | * | 7/2001 | Baker | A45C 15/06 362/154 |
| 8,672,172 B2 | * | 3/2014 | Huntington | B65D 25/04 220/523 |
| 8,911,677 B2 | * | 12/2014 | Gerstner | A61B 50/30 206/370 |
| 9,078,501 B2 | * | 7/2015 | Johnson | A45C 13/02 |
| 9,844,417 B2 | * | 12/2017 | Gerstner | A61B 50/33 |
| 10,667,965 B2 | * | 6/2020 | Pixner | A61F 17/00 |

FOREIGN PATENT DOCUMENTS

| | | | |
|---|---|---|---|
| CN | 201692273 U | * | 1/2011 |
| CN | 203263660 U | * | 11/2013 |

* cited by examiner

*Primary Examiner* — Bryon P Gehman
(74) *Attorney, Agent, or Firm* — Morland C. Fischer

(57) ABSTRACT

A first aid kit including a bottom in which to carry a first number of first aid products, a cover pivotally connected to the bottom and rotatable between closed and open positions lying over and away from the bottom, and an auxiliary tray having rotatable storage shelves at which a second number of first aid products are carried. The auxiliary tray is pivotally connected to the bottom of the first aid kit and rotatable between a folded position lying within the bottom of the kit and an unfolded position lying slightly above and to one side of the bottom to create a multi-level product storage configuration. A mounting bracket carried by the first aid kit is detached therefrom and connected to a wall. The first aid kit is reattached to the bracket, whereby the kit is suspended from the wall by the bracket.

12 Claims, 7 Drawing Sheets

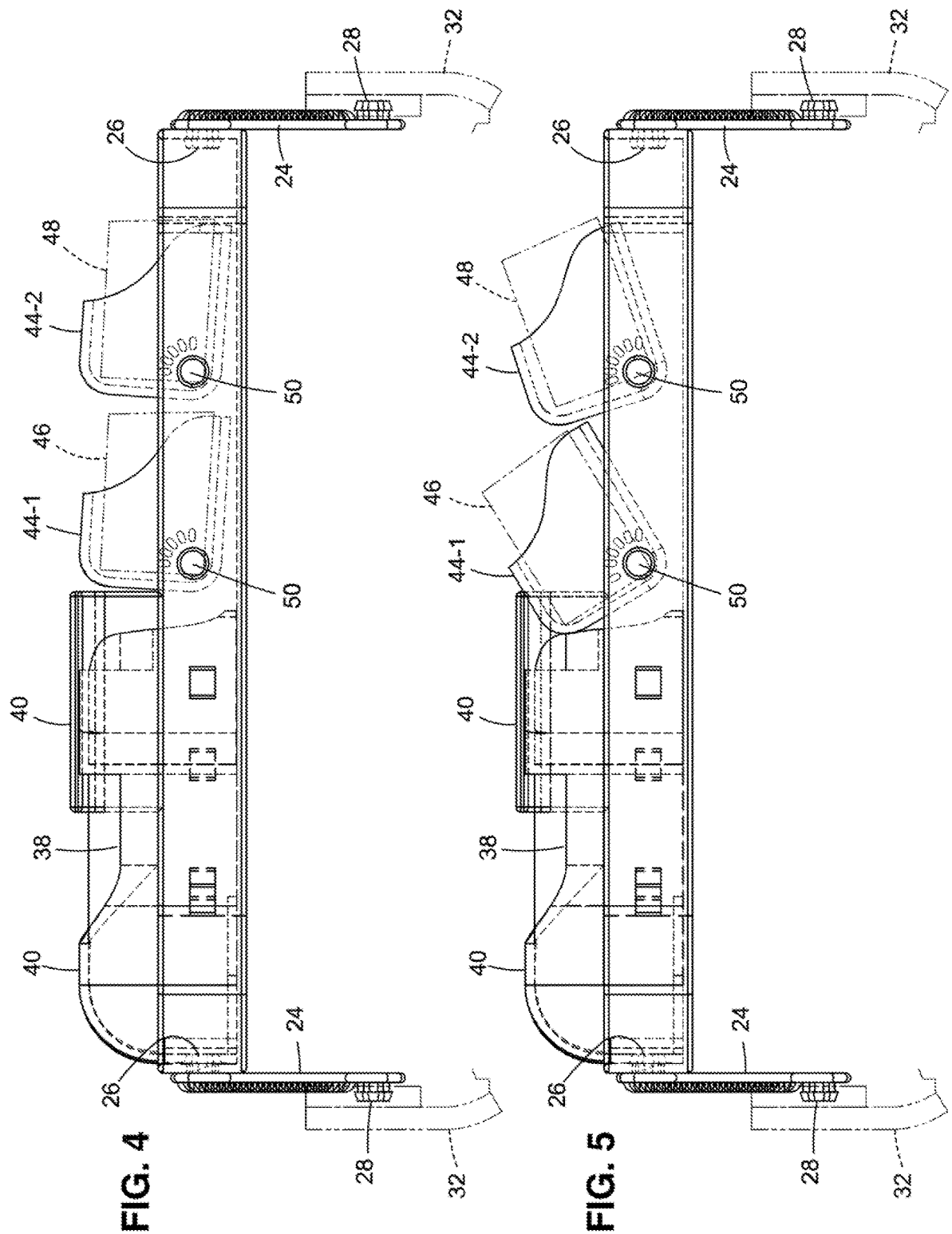

MULTI-LEVEL FIRST AID KIT AND BRACKET

BACKGROUND OF THE INVENTION

1. Field of the Invention

This invention relates to a compact, multi-level first aid kit including a bottom, a cover rotatable between open and closed positions relative to the bottom, and an auxiliary tray that is received within and rotated outwardly from the bottom when the cover is in its open position, wherein each of the bottom and the auxiliary tray has a series of product storage compartments within which a wide variety of first aid products and implements can be neatly sorted and efficiently transported in a multi-level configuration. The first aid kit carries a removable mounting bracket that can be separated therefrom and connected to a wall so that the first aid kit can be detachably connected to the bracket and suspended from the wall when it is not in use.

2. Background Art

First aid kits are well-known for providing an enclosure within which a variety of first aid products can be conveniently transported to treat a variety of ailments and injuries. It is not uncommon for the first aid products being carried within a conventional first aid kit to be mixed randomly together in no particular order. For large first aid kits, it may be difficult to find certain ones of the first aid products that may be needed for use on an urgent basis when a correspondingly large number of products are being carried in the kit and the products are all jumbled up with one another.

Accordingly, it would be desirable to have available a compact first aid kit including a plurality of storage compartments within which a large number of first aid products and implements can be neatly organized and made readily accessible to a user without the user having to waste valuable time searching through a jumbled assortment.

SUMMARY OF THE INVENTION

Disclosed herein is a compact, multi-level first aid kit having a bottom, a cover that is pivotally connected to the bottom and rotatable between open and closed positions relative to the bottom, and an auxiliary tray that is removably received within the bottom. The auxiliary tray is pivotally connected to the bottom by a pair of pivot arms so that the tray is rotatable outwardly from the bottom when the cover is first rotated to its open position. The bottom of the first aid kit includes a pair of product storage pockets. The auxiliary tray of the kit also includes a pair of product storage pockets at one end thereof and a pair of product storage shelves at the opposite end. The product storage pockets at the bottom of the first aid kit and the product storage pockets and shelves at the auxiliary tray are arranged in order to carry a variety of neatly organized first aid products and implements. When the auxiliary tray is rotated outwardly from the bottom of the first aid kit, the tray is held slightly above and to one side of the bottom so as to establish a multi-level storage configuration. To facilitate access to the first aid products carried by the product storage shelves of the auxiliary tray, the shelves are rotatable so as to project upwardly from the tray at an angle.

A mounting bracket is removably received within a recess that extends laterally across the bottom of the first aid kit. The mounting bracket can be separated from the kit and attached to a flat surface, such as a wall. The first aid kit can then be detachably connected to the mounting bracket by which it will be suspended from the wall at times when the kit is not being used.

BRIEF DESCRIPTION OF THE DRAWINGS

FIG. 4 is a side view of the auxiliary tray showing the storage shelves of FIG. 3 lying flush against the tray prior to their upward rotation;

FIG. 5 is a side view of the auxiliary tray showing the storage shelves of FIG. 3 angled relative to the auxiliary tray after their upward rotation;

DESCRIPTION OF THE PREFERRED EMBODIMENT

Figure 1:
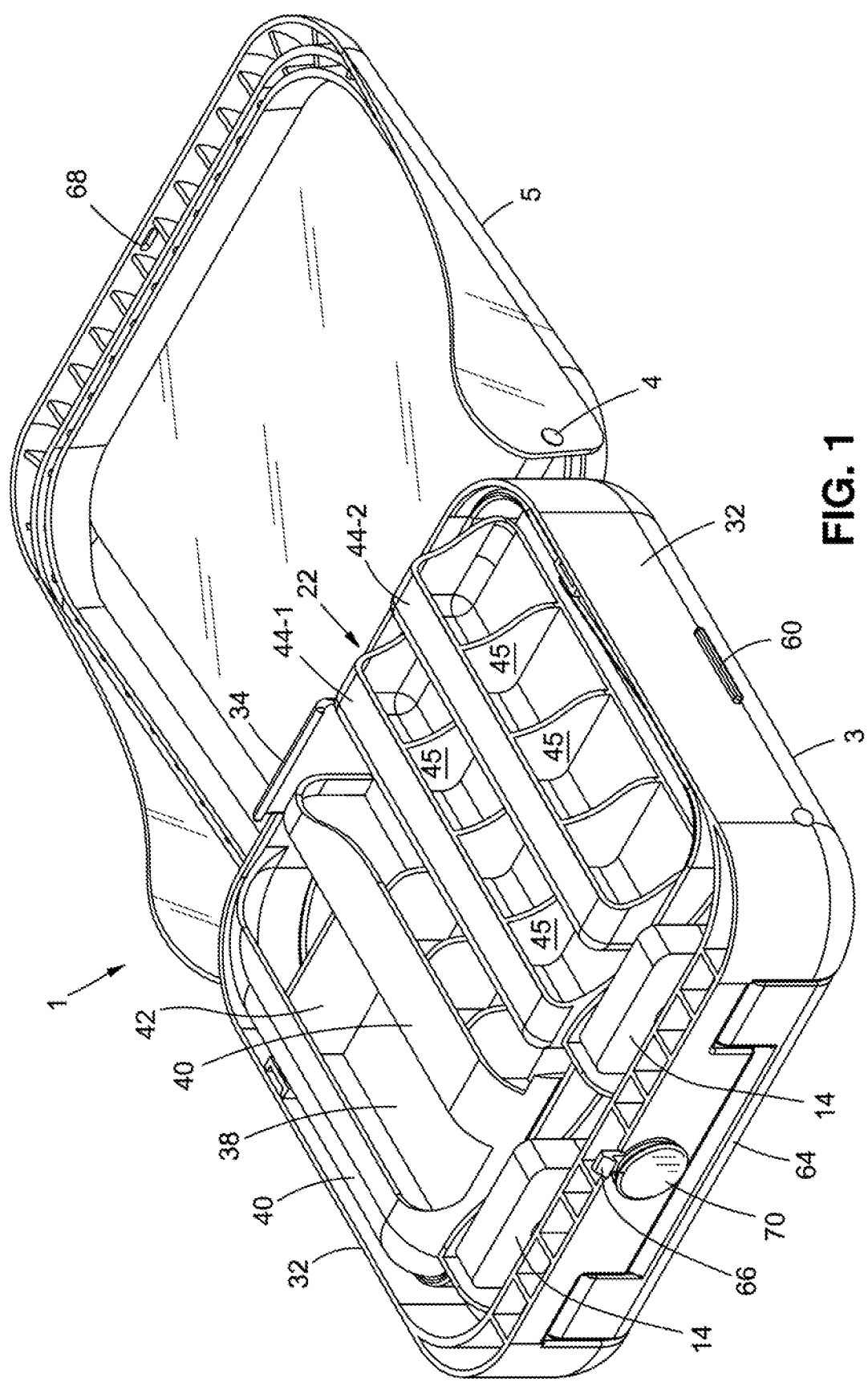
FIG. 1 is a perspective view of a compact, multi-level first aid kit according to a preferred embodiment having a bottom, an auxiliary tray located within and rotatable outwardly from the bottom, and a cover moved to an open position upwardly from and off the bottom.
Figure 2:
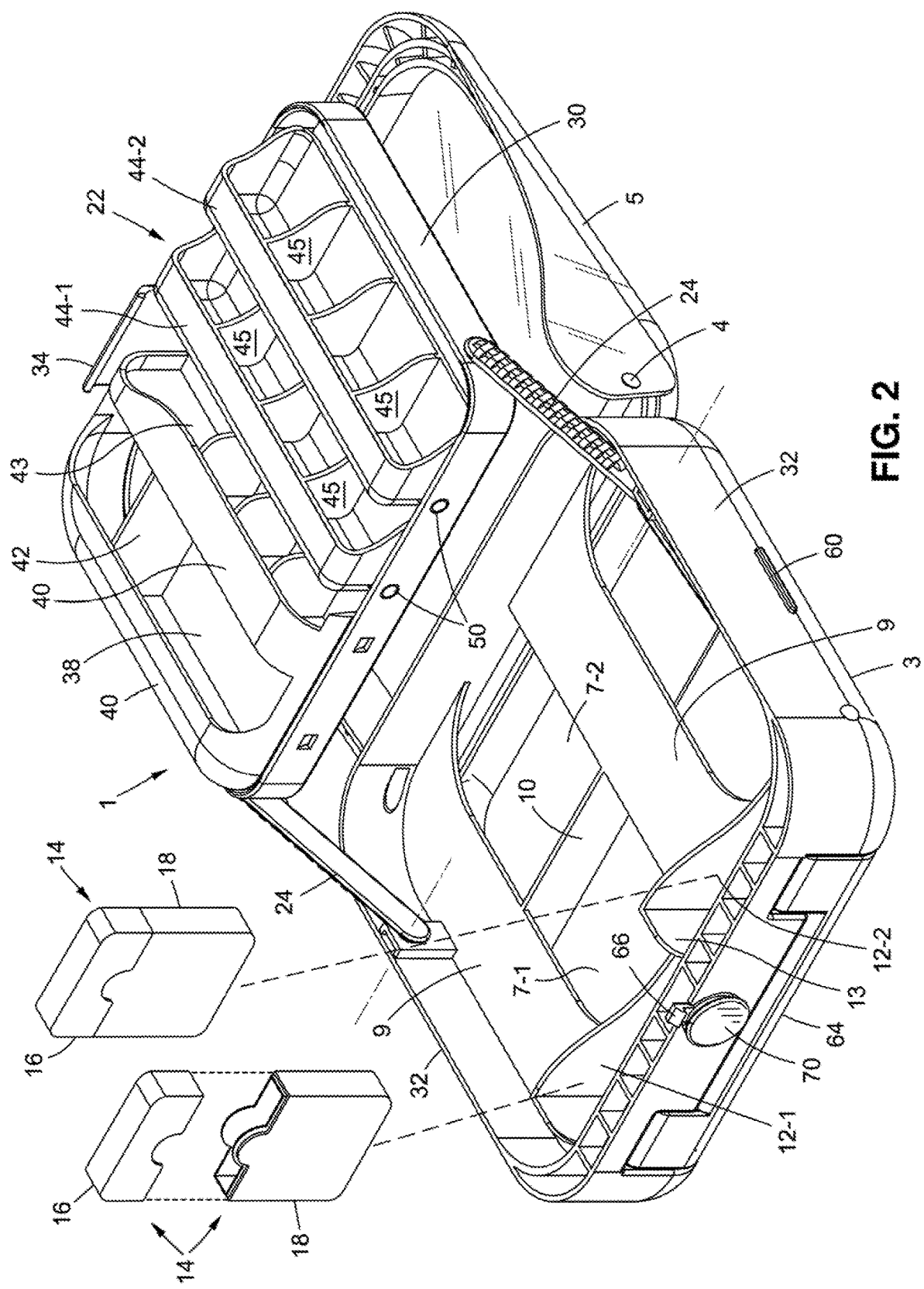
FIG. 2 shows the first aid kit of FIG. 1 wherein the auxiliary tray is rotated outwardly of and to one side of the bottom to establish a multi-level storage configuration for first aid products being carried by the kit.
Figure 3:
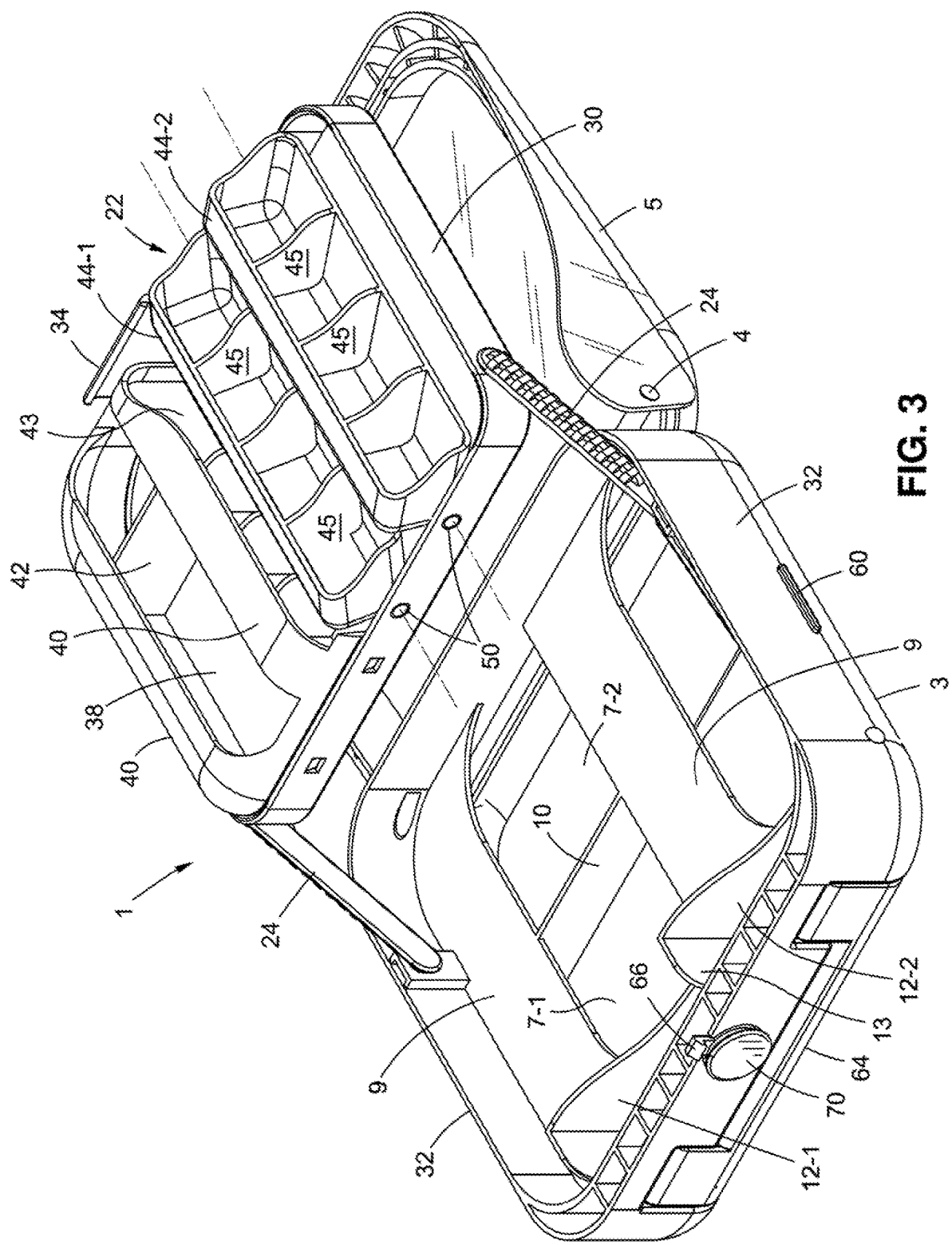
FIG. 3 shows the first aid kit of FIG. 2 wherein rotatable storage shelves that are located at one end of the auxiliary tray have been rotated upwardly relative to the tray to facilitate access to any first aid products being carried therein.

Referring initially to FIGS. 1-3 of the drawings, there is shown a compact first aid kit 1 (i.e., a carrying case) that is adapted to efficiently transport and neatly organize a wide variety of first aid products (e.g., aspirin tablets, bandages, gauze rolls, alcohol wipes, burn and wound dressings, insect sting relief, and the like) to treat a wide variety of ailments and injuries. However, it is to be understood that the particular first aid products being transported in the first aid kit 1 form no part of this invention.

The first aid kit 1 includes a generally rectangular bottom 3 and a generally rectangular cover 5 that is pivotally coupled to the bottom 3 by means of an axle 4 that runs laterally along the back of the bottom 3. Thus, the cover 5 can be rotated relative to the bottom 3 between a closed position lying over the bottom 3 and an open position moved upwardly and off the bottom 3 to permit access to the first aid products that are sorted and neatly organized within the bottom 3. Opposite ends of the axle 4 are received by respective pivot holes 6 (best shown in FIG. 9) that are formed through opposite sides of the cover 5. The bottom 3 and the cover 5 of the first aid kit 1 are manufactured from a durable, weather resistant material such as, for example, plastic or stainless steel.

A pair of adjacent product storage pockets 7-1 and 7-2 (best shown in FIGS. 2 and 3) are formed (e.g., molded) within the bottom 3 of the first aid kit 1. A corresponding pair of flat faces 9 surround the tops of the storage pockets 7-1 and 7-2 such that the pockets are recessed below the faces. The storage pockets 7-1 and 7-2 are sized to receive therewithin some of the aforementioned first aid products and/or implements (e.g., a scissors, cotton tip applicators, a cold pack, and the like) that are useful to treat an individual in need of aid. A divider wall 10 stands upwardly from the bottom 3 of the first aid kit 1 to separate the pair of product storage pockets 7-1 and 7-2 from one another.

A pair of product storage compartments 12-1 and 12-2 are located at the bottom 3 of the first aid kit 1 in front of the storage pockets 7-1 and 7-2. The compartments 12 which lie side-by-side are separated from one another by a divider 13 in order to receive therewithin a corresponding pair of removable cases 14 (best shown in FIG. 2). The cases 14 which ideally carry commercially available first aid products (e.g., adhesive bandages or medication packets) and may be conveniently removed from their compartments 12 in bottom 3 of the first aid kit 1 and carried in one's pocket independently of their also being carried within the first aid kit. To this end, each removable case 14 has a lid 16 that is slidable upwardly and off the bottom 18 to the case 14 to permit a user to gain easy access to and use whatever first aid product is being carried in the case 14 at a location that is remote from the kit 1.

Figure 9:
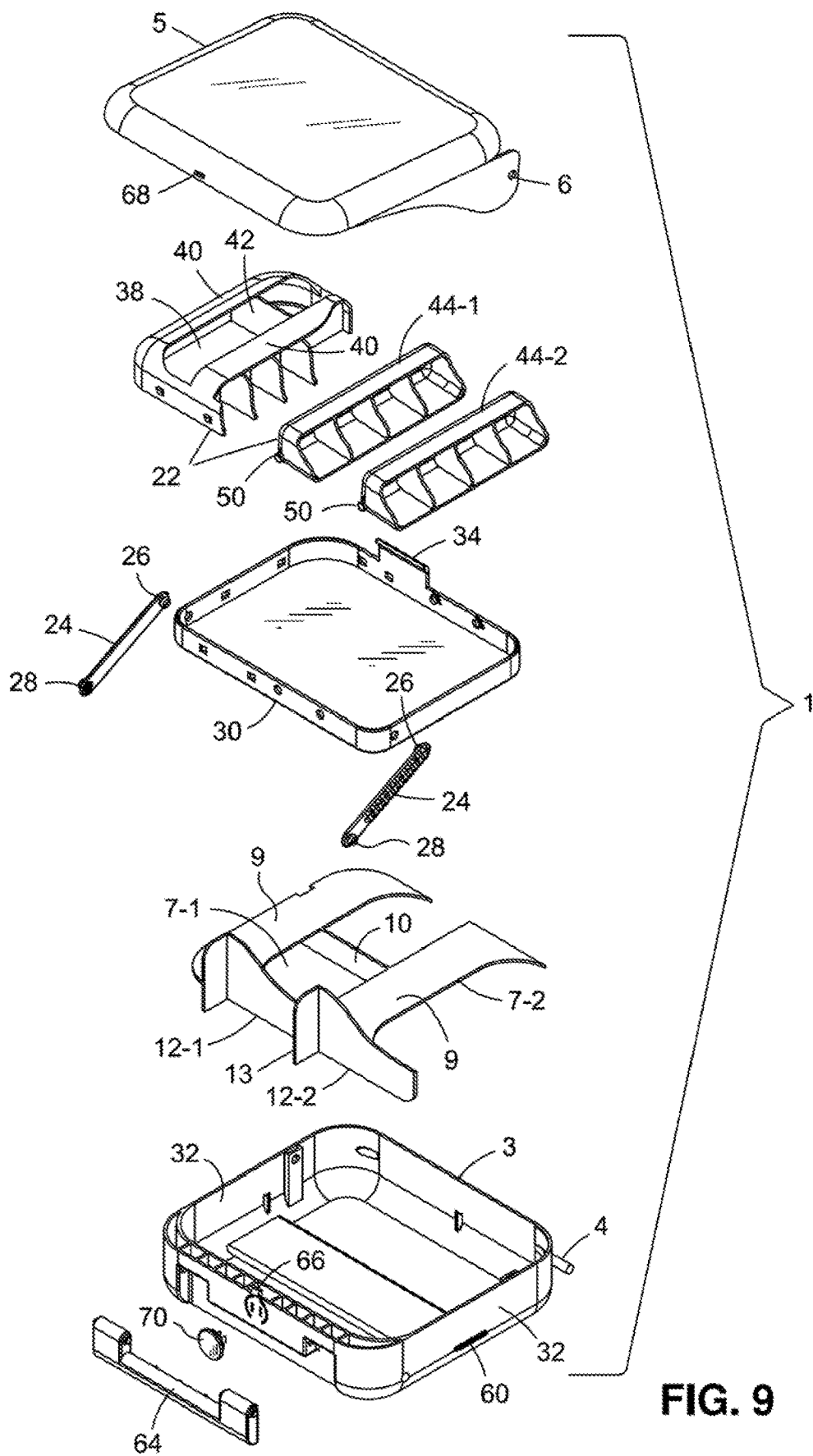
FIG. 9 is an exploded view of the first aid kit shown in FIGS. 1-8.

Located between the bottom 3 and the cover 5 of the first aid kit 1 is an auxiliary tray 22 that is pivotally connected and rotatable relative to the bottom 3 by means of a pair of pivot arms 24 that extend between pivots 26 at first ends of the arms 24 and pivots 28 at the opposite ends of the arms 24 (best shown in FIG. 9). The first ends of the pivot arms 24 are pivotally connected by means of the pivots 26 to a collar 30 that surrounds the auxiliary tray 22, and the opposite ends of the pivot arms 24 are pivotally connected by means of the pivots 28 to walls 32 located at opposite sides of the bottom of the first aid kit 1. With the cover 5 of the first aid kit 1 rotated in a downward direction to its closed position at which to lie over the bottom 3, the kit 1 can be transported from place-to-place or stored during times of non-use. Prior to the cover 5 being closed, the auxiliary tray 22 is rotated by its pivot arms 24 towards its receipt within the bottom of the kit so as to be seated in a folded position upon the flat faces 9 that surround the recessed product storage pockets 7-1 and 7-2. In its folded position, the auxiliary tray 22 will lie adjacent the storage compartments 12-1 and 12-2 located in the bottom 3 of the kit 1 within which the removable cases 14 are carried.

After the cover 5 of the first aid kit 1 has been rotated in an opposite upward direction to its open position and moved away from and off the bottom 3 of the kit to permit access to the contents thereof, the auxiliary tray 22 may be rotated by the pivot arms 24 outwardly from the bottom 3 to an unfolded position. In this case, the auxiliary tray 24 will lie slightly above and alongside the bottom of the first aid kit 1 to permit access to any first aid products and implements that are carried by the bottom 3 and the tray 24 of kit 1 (best shown in FIGS. 2 and 3). Thus, the first aid kit 1 is provided with a multi-level storage configuration to enable a larger number of first aid products and implements to be carried and selectively accessed than those associated with conventional single tier kits.

Standing upwardly from the collar 30 that surrounds the auxiliary tray 22 is an integral pull tab 34. The pull tab 34 is accessible to a user to be grasped and pulled upwardly, whereby to lift the auxiliary tray 22 upwardly and outwardly from its receipt within the bottom 3 of the first aid kit 1 and thereby enable the user to easily rotate the auxiliary tray 22 from its folded position of FIG. 1 to its unfolded position of FIGS. 2 and 3.

Referring concurrently now to FIGS. 1-4 of the drawings, the auxiliary tray 22 of the first aid kit 1 is shown having a product storage pocket 38 formed (e.g., molded) at one end thereof. A flat face 40 surrounds the top of the storage pocket 38 such that the pocket 38 is recessed below the face. An upstanding end wall 42 and an upstanding side wall 43 lie below the face 40 and across the storage pocket 38 so that first aid products or implements may be carried by the first aid kit within the confines of pocket 38.

Located at the end of the auxiliary tray 22 that lies opposite the product storage pocket 38 are a pair of pivotal product storage shelves 44-1 and 44-2 lying one next to the other. Each storage shelf 44-1 and 44-2 is divided by spaced, parallel walls 45 into a plurality of small shelf sections in which correspondingly small first aid products (shown in phantom lines and designated 46 and 48 in FIGS. 4 and 5) can be carried. As an important feature of the first aid kit 1, the storage shelves 44-1 and 44-2 are rotatable relative to the auxiliary tray 22 to enable a user to gain easy access to and insert or remove the products 46 and/or 48 from the shelves.

That is, the opposite ends of each product storage shelf 44-1 and 44-2 are coupled to the collar 30 that surrounds the auxiliary tray 22 by means of respective pivots (only one of which 50 being shown). By virtue of the foregoing, either one or both of the storage shelves 44-1 and/or 44-2 is rotatable around its pivots 50 between a product carrying position lying substantially horizontal relative to and flush against the auxiliary tray 22 (best shown in FIG. 4) and a product access position angled upwardly relative to the auxiliary tray 22 (best shown in FIG. 5).

Figure 6:
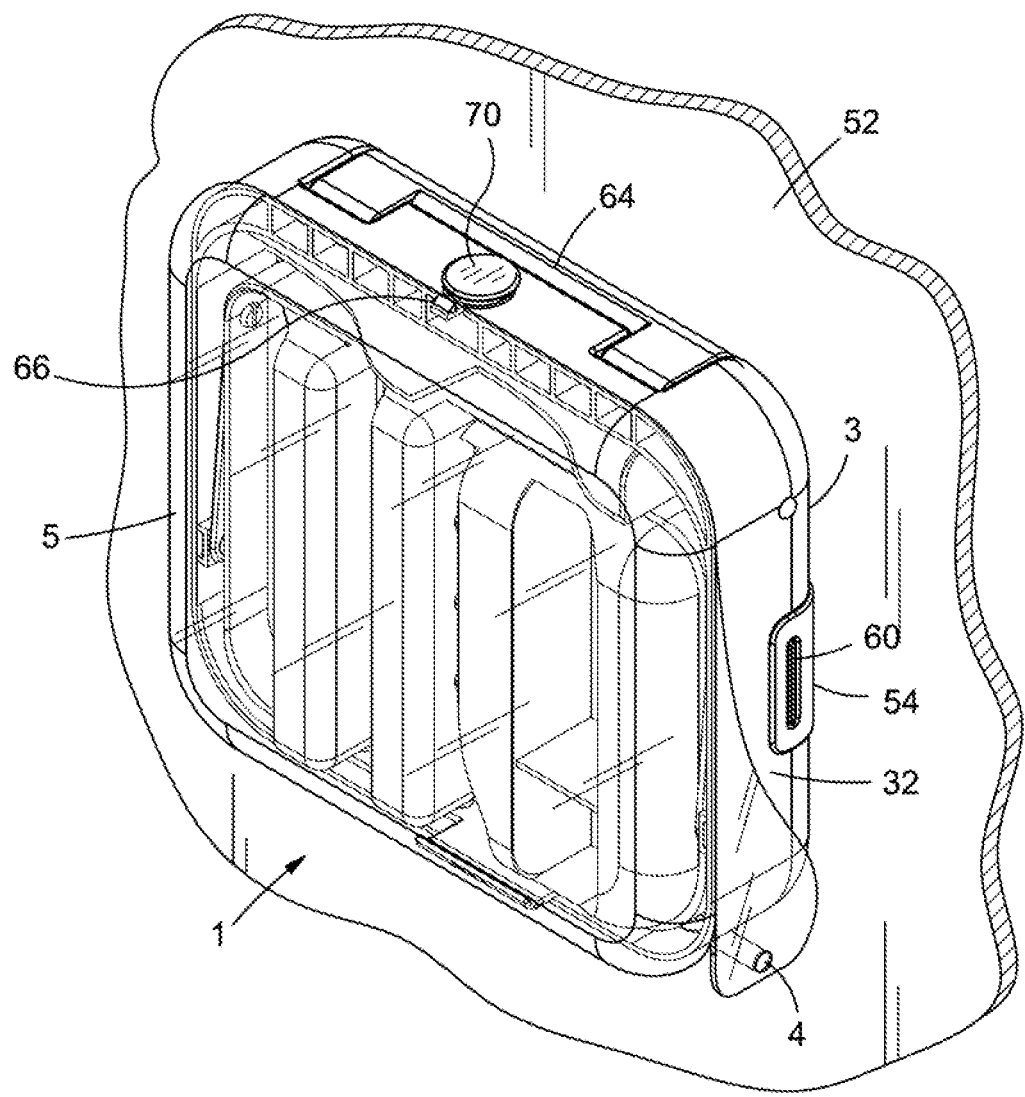
FIG. 6 shows the first aid kit of FIG. 1 with the cover thereof moved to a closed position lying over the bottom of the kit with the kit suspended from a wall when it is not in use.
Figure 7:
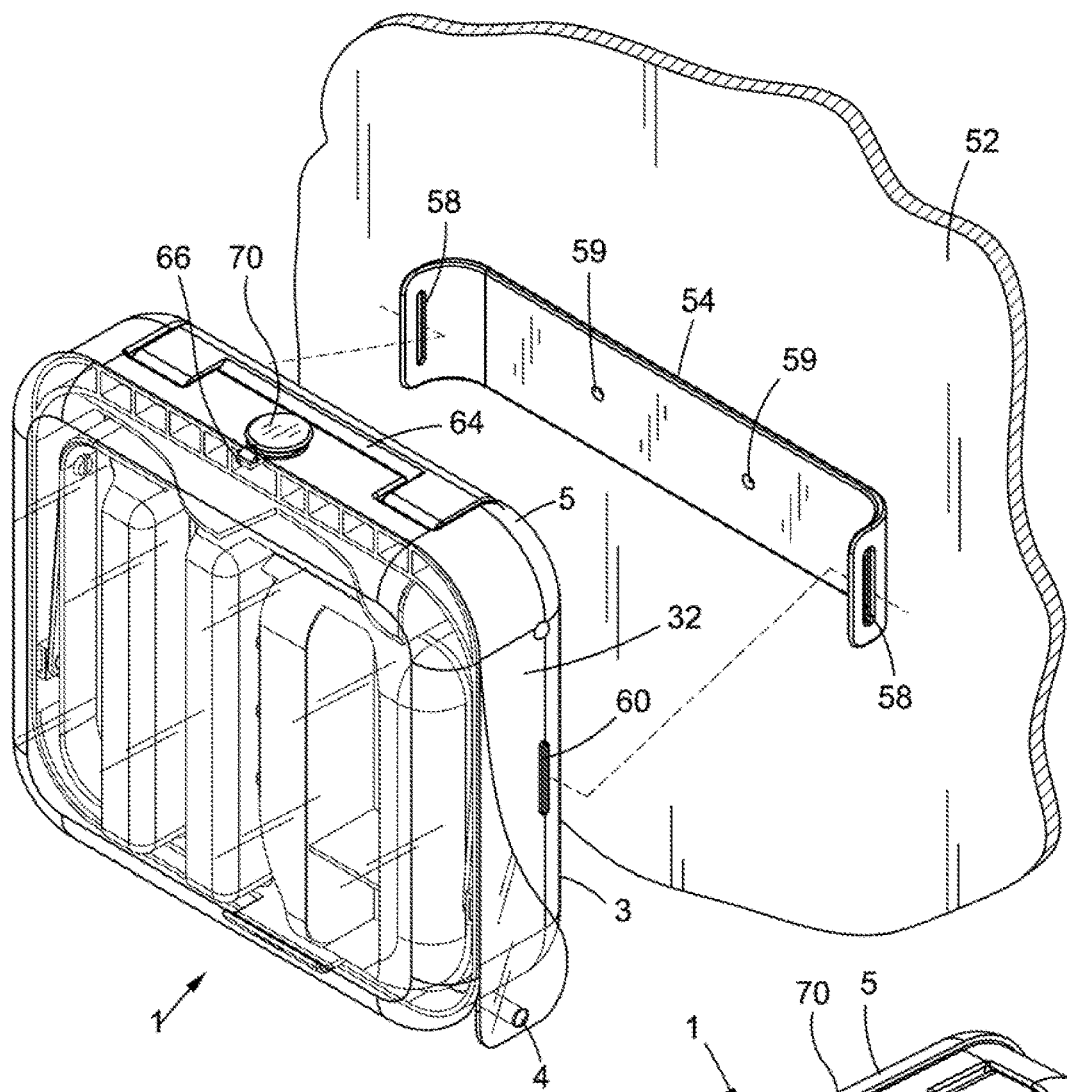
FIG. 7 shows the first aid kit of FIG. 6 being detachably connected to a mounting bracket that is attached to the wall from which the kit is to be suspended.
Figure 8:
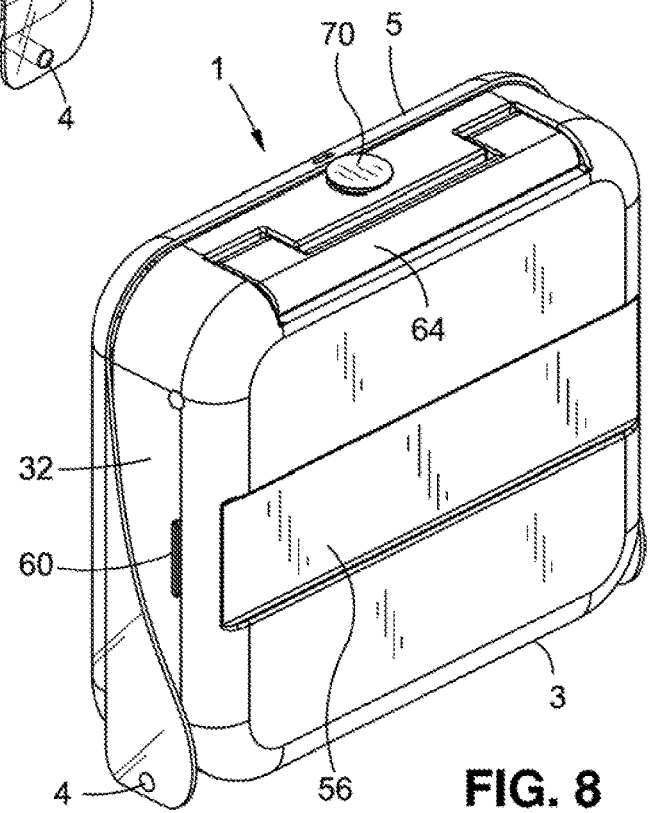
FIG. 8 shows a recess formed in the bottom of the first aid kit within which the mounting bracket of FIG. 7 is removably received.

Another important feature of the first aid kit 1 is now explained while referring to FIGS. 6-8 of the drawings, wherein means are described for detachably connecting the kit to a flat surface 52 (e.g., a wall) at which the kit can be located during times of none-use. More particularly, a flexible U-shaped mounting bracket 54 is removably attached to the first aid kit 1 for receipt within a recess 56 (best shown in FIG. 8) that runs laterally across the bottom 3 of the kit. The opposite ends of the mounting bracket 54 are bent to turn upwardly and engage the sidewalls 32 of the bottom 3 of the kit 1. A mounting slot 58 (best shown in FIG. 7) is formed through each of the bent upturned ends of the mounting bracket 54. A pair of mounting holes 59 are formed through the mounting bracket 54 between the bent opposite ends thereof.

A bracket retaining tab 60 extends outwardly from each of the opposite side walls 32 of the bottom 3 of the first aid kit 1. When the kit 1 is in use for treating an individual in need of care, the mounting bracket 54 is located within the recess 56 that runs laterally across the bottom 3, and the bracket retaining tabs 60 which project from the side walls 32 of the bottom 3 are removably received (i.e., snap-fit) within respective ones of the mounting slots 58 that are formed in the bent ends of bracket 54.

During those times when the first aid kit 1 is not being used, the U-shaped mounting bracket 54 can be removed from the recess 56 located at the bottom 3 of the kit and fastened to the wall 52 or similar flat surface. Because of its flexible nature, the bent ends of the bracket 54 can be pulled outwardly and flexed in opposite directions so that the bracket retaining tabs 60 at the side walls 32 of the bottom 3 are separated from the mounting slots 58 formed in bracket

54. Fasteners (not shown) are inserted through the mounting holes 59 by which to connect the bracket 54 to the wall 52. The first aid kit 1 may now be hung from the mounting bracket 54 and suspended from the wall 52 by pushing the kit against the bracket until the bracket retaining tabs 60 at side walls 32 are once again snap fit within the mounting slots 58 formed in the opposite upturned ends of the bracket 54.

When it is necessary, the first aid kit 1 can be pulled away from and detached from the mounting bracket 54 to be used while the bracket remains still attached to the wall 52. To this end, the first aid kit 1 includes a rotatable handle 64 pivotally connected to the bottom 3 of the kit at the front thereof. A latch closure 66 stands upwardly from the bottom 3 above the handle 64 to engage the front of the cover 5 of the kit at a notch 68 (best shown in FIGS. 1 and 9) formed therein. The latch closure 66 holds the cover 5 of the first aid kit 1 in its closed position over the bottom 3 as shown in FIGS. 6-8. A push-button 70 is located at the front of the bottom 3 above the latch closure 66 to receive a pushing force thereagainst and thereby move the latch closure 66 out of its engagement with the notch 68 so that the top of the kit 1 can be rotated off the bottom 3 and moved to its open position as shown in FIGS. 1-3.

FIG. 9 of the drawings illustrates an exploded view of the first aid kit as shown in and described while referring to FIGS. 1-8. FIG. 9 shows the bottom 3 and the cover 5 of the kit 1 separated from one another with the rotatable auxiliary tray 22 lying therebetween for conveniently transporting, organizing and making readily accessible a wide variety of first aid products and implements as previously explained.

The invention claimed is:

1. A first aid kit in which to transport first aid products, said first aid kit having opposite side walls and comprising:
    a bottom having at least one first aid product storage compartment within which to carry a first number of first aid products;
    a top being movable between a first position lying over said bottom and a second position away from and off said bottom;
    an auxiliary storage tray removably received within said bottom and having at least one first aid product storage compartment in which to hold a second number of first aid products, said auxiliary storage tray being movable between a first position lying within said bottom and above the at least one first aid product storage compartment of said bottom and a second position located outwardly from said bottom and away from the at least one first aid product storage compartment of said bottom when said top is moved to the second position thereof; and
    a bracket attached to said first aid kit, said bracket capable of being detached from said first aid kit and connected to a flat surface, and said first aid kit being reattachable to said bracket so that said first aid kit is suspended from the flat surface by means of said bracket,
    wherein said first aid kit has a respective bracket retaining tab located at each of the side walls of the first aid kit, said bracket being flexible and having a respective mounting slot formed in each of opposite ends, said bracket being removably attached to said first aid kit when said bracket retaining tabs are received by respective ones of said mounting slots.

2. The first aid kit recited in claim 1, wherein said auxiliary storage tray is pivotally connected to the bottom of said first aid kit such that said auxiliary storage tray is rotatable relative to said bottom between the first and second positions of said auxiliary storage tray.

3. The first aid kit recited in claim 2, wherein said auxiliary storage tray is pivotally connected to the bottom of said first aid kit by means of a pair of pivot arms extending therebetween, such that said auxiliary storage tray is rotated to the second position thereof at which to lie above and at one side of said bottom to establish a multi-level storage configuration.

4. The first aid kit recited in claim 1, wherein said auxiliary storage tray also has at least one product storage shelf on which to carry a third number of first aid products.

5. The first aid kit recited in claim 4, wherein said at least one product storage shelf is pivotally connected to said auxiliary storage tray so as to be rotatable between a first position lying horizontally with respect to said auxiliary storage tray and a second position angled upwardly with respect to said auxiliary storage tray.

6. The first aid kit recited in claim 4, wherein the at least one product storage shelf of said auxiliary storage tray is divided into a plurality of shelf sections wherein each one of said plurality of shelf sections is located side-by-side a successive one of said plurality of shelf sections.

7. The first aid kit recited in claim 1, wherein the bottom of said first aid kit has a second first aid product storage compartment and a product enclosing case removably received within said second first aid product storage compartment to be removed from said second compartment and separated from said first aid kit, said product enclosing case having a removable lid.

8. The first aid kit recited in claim 1, wherein the at least one first aid product storage compartment of the bottom of said first aid kit is a pocket that is surrounded by a flat face lying above said pocket such that said pocket is recessed with respect to the flat face surrounding said pocket.

9. The first aid kit recited in claim 1, wherein said bracket is carried by said first aid kit within a recess formed in the bottom of said first aid kit.

10. The first aid kit recited in claim 1, wherein said bracket has a U-shape with said opposite ends being upturned said U-shaped bracket engaging and surrounding the bottom and opposite side walls of said first aid kit, and each of the upturned opposite ends of said U-shaped bracket having one of said mounting slots formed therein.

11. A carrying case for transporting products therewithin and configured to be suspended from a flat surface, said carrying case having opposite side walls and comprising:
    a bottom having at least one storage compartment within which to receive and transport products,
    a top being movable between a first position lying over the at least one storage compartment of said bottom and a second position away from and off said bottom; and
    a U-shaped bracket removably attached to the bottom and to the side walls of said carrying case, said U-shaped bracket being detachable from said bottom and from the opposite side walls of said carrying case to be connected to the flat surface at which to be reattached to the bottom and to the opposite side walls of said carrying case such that said carrying case is suspended from the flat surface by means of said U-shaped bracket,
    wherein said carrying case has a recess formed in the bottom thereof and extending laterally thereacross, said recess being sized to removably receive said U-shaped bracket therewithin by which to enable said U-shaped bracket to be removably attached to the bottom and to the opposite side walls of said carrying case.

12. The carrying case recited in claim 11, further comprising a bracket retaining tab located at each of the opposite side walls of said carrying case, said U-shaped bracket being flexible and having opposite ends and a mounting slot formed in each of said opposite ends of the U-shaped bracket, said U-shaped bracket being removably attached to said carrying case when said U-shaped bracket is removably received within the recess of said carrying case and said bracket retaining tabs are received by respective ones of said mounting slots.

\* \* \* \* \*